United States Patent [19]
Chou

[11] Patent Number: 5,373,723
[45] Date of Patent: Dec. 20, 1994

[54] APPARATUS FOR DETERMINING FRICTION BETWEEN A SUPPORT ROLLER AND A RUBBER ROLLER

[76] Inventor: Shou-Lai Chou, No. 35-19, Hsia-Kuo Ln., Tai-Ping Rd., Ta-Li Hsiang, Taichung, Taiwan, Prov. of China

[21] Appl. No.: 943,626

[22] Filed: Sep. 11, 1992

[51] Int. Cl.$^5$ .................. G01N 3/56; G01N 19/02
[52] U.S. Cl. .................................. 73/9; 73/159; 271/263
[58] Field of Search .............. 73/9, 159; 271/258, 271/262, 263, 265, 270; 346/134; 355/93

[56] References Cited

U.S. PATENT DOCUMENTS

| | | | |
|---|---|---|---|
| 3,360,978 | 1/1968 | Shinn | 73/9 |
| 3,902,363 | 9/1975 | Ishimoto | 73/159 |
| 4,453,404 | 6/1984 | Powell et al. | 73/159 |
| 4,494,747 | 1/1985 | Graef et al. | 271/263 |
| 4,632,718 | 12/1986 | Shimizu | 271/262 |
| 4,938,071 | 7/1990 | Kobayashi et al. | 73/159 |
| 5,116,035 | 5/1992 | Russel et al. | 271/265 |

Primary Examiner—Richard E. Chilcot, Jr.
Assistant Examiner—William L. Oen
Attorney, Agent, or Firm—Browdy and Neimark

[57] ABSTRACT

An apparatus for determining friction between a support roller and a rubber roller comprising an adjustable horizontal seat board, a pivoted stand supporting a pivot spindle in parallel to the seat board, an adjustable horizontal pressure pad for applying even downward pressure, a clamping and driving assembly for clamping two ends of the rubber roller, a support roller for supporting one end of the paper, a paper holding device with rollers below for holding the other end of the paper, a load cell in connection with the paper holding device for conveying a pull from generated friction, and a set of weights for selecting to be placed on the horizontal pressure pad. In use, the rubber roller, evenly pressing on one end of the paper, may be driven into turning at a fixed speed to allow a relatively accurate frictional factor to be detected.

1 Claim, 2 Drawing Sheets

APPARATUS FOR DETERMINING FRICTION BETWEEN A SUPPORT ROLLER AND A RUBBER ROLLER

FIELD OF THE INVENTION

The present invention relates to an apparatus for determining friction between a support roller and a rubber roller, and particularly to a new one designed to detect the frictional factor generated in any kind of the paper-transmitting machine to bring about a paper transmission with better reliability.

BACKGROUND OF THE INVENTION

In today's photocopier, fax machine, printer, money machine and automatic selling machine, transmission of paper or bank notes merely takes advantage of the friction generated between the rubber roller and the paper to be fed. However, the machine's reliability is questioned. Up until the present invention, the standardization of the frictional factor was still found to be difficult, and consequently the production of a properly fitting rubber roller was difficult to achieve. Reliability seems to be obtainable only with numerous tests. As for determining the frictional factor, a spring scale capable of measuring how much force is used to pull out a paper sheet held between rubber rollers is conventionally used. The frictional factor (u) could then be calculated by dividing the measured force by the pressure exerted between rubber rollers. Although simple, the test result will be in a wide error range due to difficulty in maintaining a fixed pulling seed.

OBJECTS OF THE INVENTION

In order to solve the above-mentioned problem, the present invention provides an apparatus for determining friction between a support roller and a rubber roller whose features include:
1. Two ends of the roller are clamped below a horizontal pressure pad of a pivoted stand, with the rubber roller in parallel to the horizontal pressure pad. As a preset burden is placed on a sideboard of horizontal pressure pad which opposes the rubber roller, the rubber roller positioned below the horizontal pressure pad is caused to lower and horizontally press one end of the paper.
2. One end of the paper is put on a support roller which is in its horizontal state, whereas the other paper end is held and connected with a load cell.
3. Driving of the rubber roller is performed by a speed-fixed motor.

SUMMARY OF THE INVENTION

An apparatus for determining friction between a support roller and a rubber roller comprises an adjustable horizontal seat board, a pivoted stand supporting a pivot spindle in parallel to the seat board, an adjustable horizontal pressure pad for applying even downward pressure, a clamping and driving assembly for clamping two ends of the rubber roller and for turning it at a fixed speed, a support roller for supporting one end of the paper, a paper holding device with rollers for holding the other end of the paper, a load cell in connection with the paper holding device to convey a pull from the generated friction of the rubber roller against the paper, and a set of weights for selecting to be placed on the horizontal pressure pad. In use, the rubber roller, evenly pressing on one end of the detection-ready paper, may be driven into turning at a fixed speed to allow a relatively accurate frictional factor to be detected.

SPECIFIC DESCRIPTION

Figure 1:
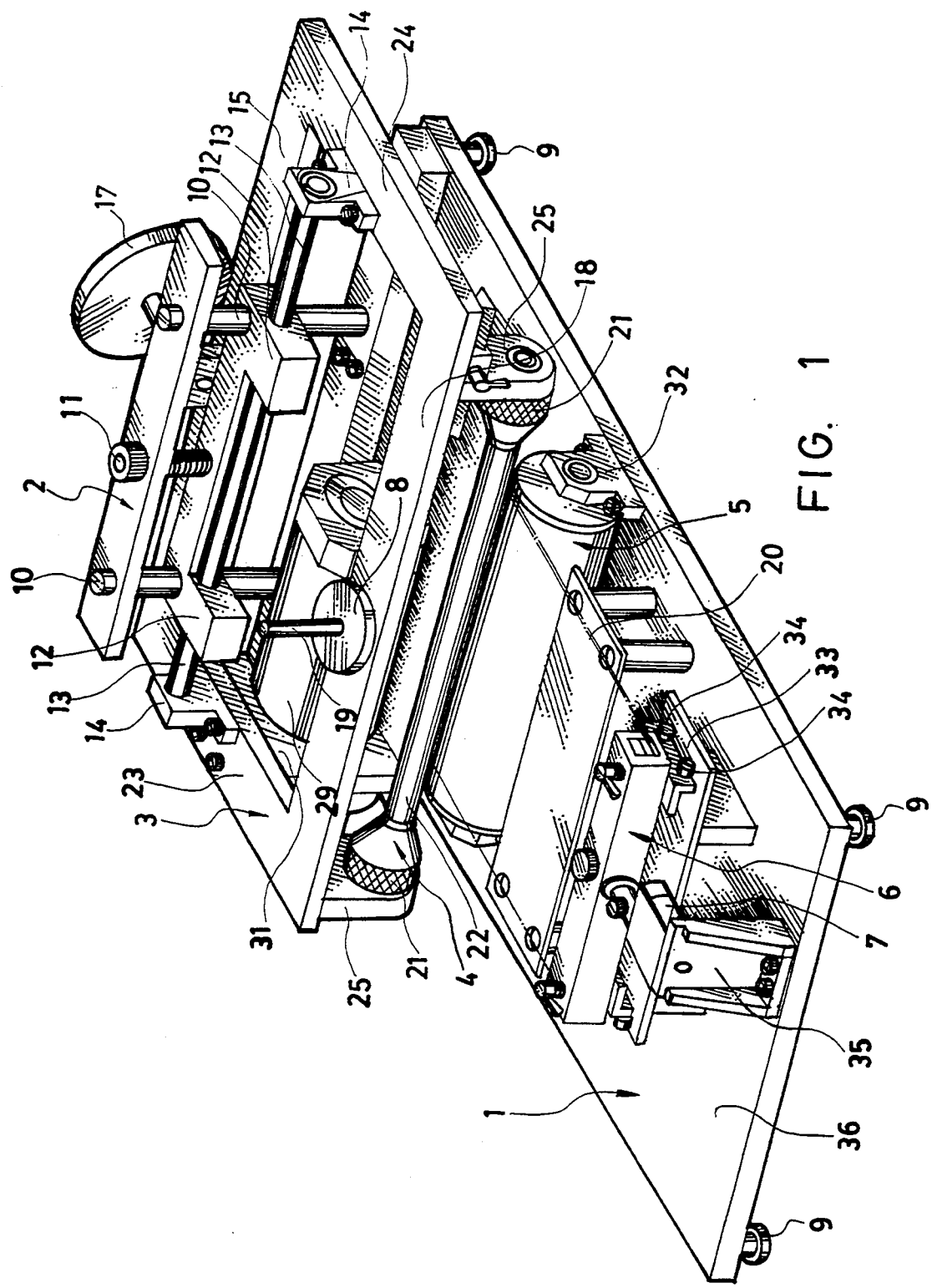
FIG. 1 is a perspective, oblique view of the invention with the detection meter not shown.
Figure 2:
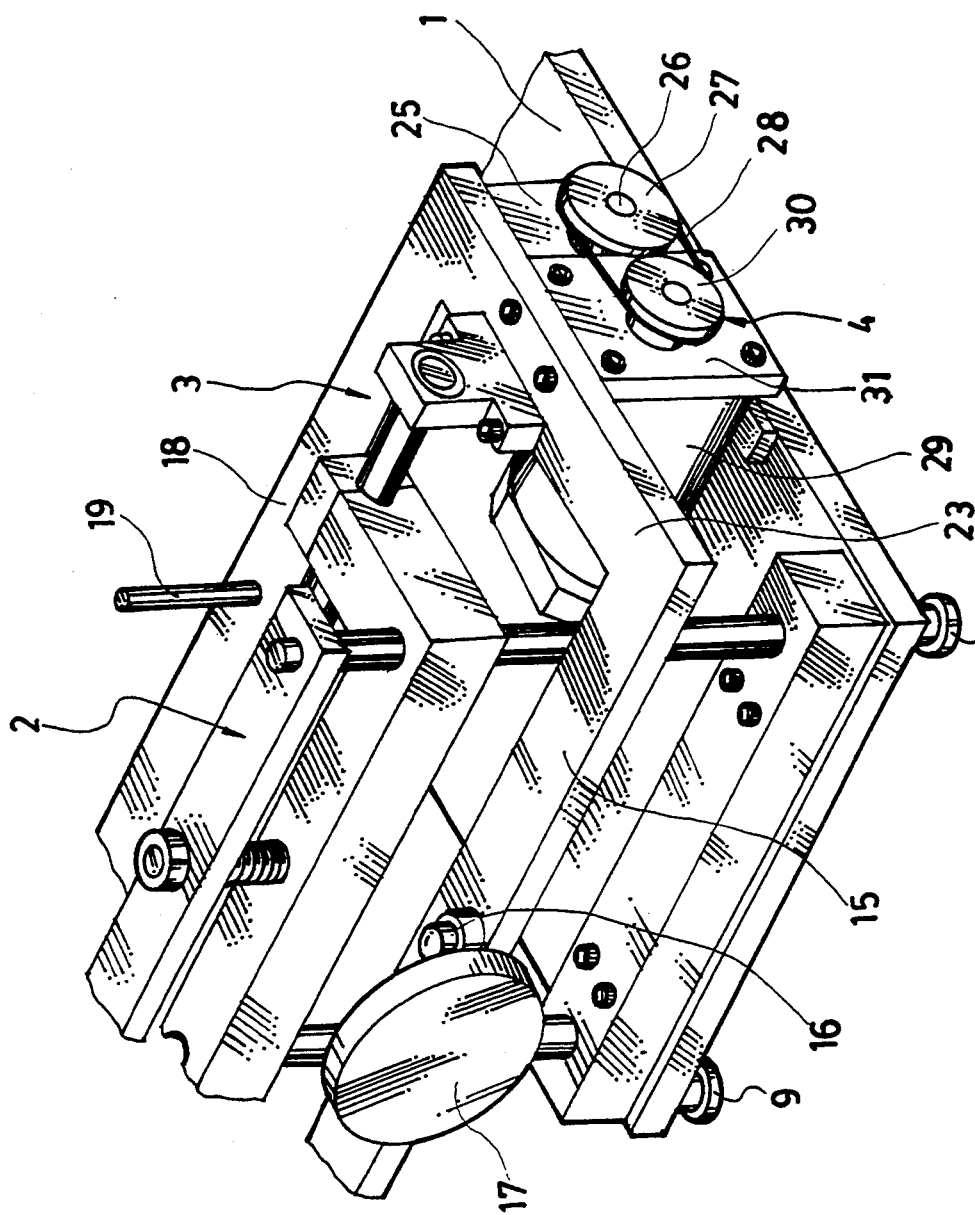
FIG. 2 is a locational, oblique view of FIG. 1 taken from another direction.

As FIGS. 1 and 2 show, this invention comprises a seat board 1, a pivoted stand 2, a horizontal pressure pad 3, a clamping and driving assembly 4, a support roller 5, a paper holding device 6, a load cell 7 and weights 8. Seat board 1 is a rectangular planar board arranged with legs 9 at the angular positions to allow adjustment of its upper side thereof into a horizontal state. At one end of the upper side of seat board 1 a pivoted stand 2 is connected by two supports 10 vertically fixed on board to string a pivot spindle base 12 made adjustable in altitude by means of an adjusting screw 11. A pivot spindle 13 connected to pivot spindle base 12 keeps in parallel to seat board 1. Each end of pivot spindle 13 is pivoted in a spindle sleeve 14 fixed in the middle of the third and forth sideboards 23, 24 of a horizontal pressure pad 3. Horizontal pressure pad 3 is a planar, frame-like board arranged with a level vial 16 in the middle of the upper side of its first sideboard 15 thereof and a balance screw 17 nearby to allow for adjustment of the horizontal pressure pad into a horizontal state when no weight(s) is put on its second sideboard 18 thereof. An inserted pin 19 that holds weights 8 selected in accordance with the material of the paper 20 is in the middle of the upper side of the second sideboard 18. Beneath the ends of second sideboard 18 where a pair of pivot connection bases 25 are provided, a pair of clamping fixtures 21 are pivotally connected to bases 25 to clamp the two ends of the detection-ready rubber toller 22. A pivot spindle 26 extending out from one side of a clamping fixture 21 is connected with a follower pulley 27. An acting pulley 30 is connected with follower pulley 27 through a conveyor belt 28. Acting pulley 30 is turned by a speed-fixed motor 29 positioned on a fixing board 31 below the third sideboard 23 or horizontal pressure pad 3.

As FIG. 1 shows, a support roller 5 for supporting one end of the paper 20 is connected pivotally by a pair of axle beds 32 on seat board 1 below the second sideboard 18 of horizontal pressure pad 3. Support roller 5 is a freely turnable roller in parallel to seat board 1. The other end of the paper 20 is held by a paper holding device 6 placed on a planar stage 33 on seat board 1. Paper holding device 6 which has rollers 34 below to contact with plane stage 33 may be displaced by a pull from a generated friction of the rubber roller 22 against paper 20. The back side of paper holding device 6 is connected with a load cell 7 positioned on a fixing seat board 35 to convey the pull. A detection meter (not shown) that connects load cell 7 through a power lead 26 reveals the read value of the pull.

Before use, seat board 1 must be adjusted into a horizontal state, both rubber roller 22 and paper 20 must be firmly held, and level vial 16 must indicate that horizontal pressure pad 3 is in a horizontal state following adjustment with balance screw 17. Then suitably selected weights are placed over for sheathing weights 8 inserted pin 19 located in the middle of the upper side of second sideboard of horizontal pressure pad 3. The lowering of second sideboard 18 then will cause rubber roller 22, positioned below it, to come down to horizontally press the end of the paper 20 on support roller 5. Subsequently, speed-fixed motor 29 is started with turns rubber roller 22 at a fixed speed. Paper holding device 6 which holds the other end of paper 20 will then be displaced by a pull caused by the generated friction between the rubber roller 22 and paper 20 until the pull reaches a balance with load cell 7. When paper 20 stays still, the read value of the pull is recorded from the detection meter. The value of frictional factor (u) may be calculated as:

Resistance (detection meter's read value)/Pressure (weight)=u

I claim:

1. An apparatus for determining friction between a support roller and a rubber roller while pulling different paper items, comprising:

a planar seat board (1) having legs (9) below for adjustment of an upper side of said seat board (1) into a horizontal state, two vertical supports (10) fixed on said seat board (1), a stand (2) fixed to said vertical supports (10) above said seat board (1), a pivot spindle base (12) slidably mounted on said two vertical supports (10) below said stand (2), said pivot spindle base (12) adjustably engaged to said stand (2) by an adjusting screw (11) for adjusting an altitude of said pivot spindle base (12) relative to said stand (2), a pivot spindle (13) fixed to said first spindle base (12) parallel to said seat board (1), a planar, frame-like horizontal pressure pad having a first sideboard (15), a second sideboard (18), a third sideboard (23) and a fourth sideboard (24), a spindle sleeve (14) fixed in the middle of the third sideboard (23) and the fourth sideboard (24), each said spindle sleeve (14) pivotally connected with said pivot spindle (13), a level vial (16) arranged in the middle of the upper side of the first sideboard (15) and balance screw means (17) for adjusting the horizontal pressure pad into a horizontal state with no weight on said pressure pad, an inserted pin fixed at the middle of the upper side of the second sideboard for holding selected weights, a pair of pivot connection bases provided beneath two ends of the second sideboard, a pair of clamping fixtures, each respectively engaged to said pair of pivot connection bases to clamp the two ends of a rubber roller, end of said pivot spindle extending out from one side of said clamping fixtures and connected pivotally with a follower pulley, said follower pulley connected to an acting pulley by a conveyor belt, said acting pulley being rotated by a speed-fixed motor positioned below said horizontal pressure pad, a support roller (5) connected pivotally by a pair of axle beds on said seat board below said second sideboard of said horizontal pressure pad for supporting one end of paper being tested between said support roller and said rubber roller;

said support roller freely turnable and parallel to said seat board;

a paper holding device located on a planar stage on said seat board to the other end of said paper; said paper holding device having rollers below to contact with said planar stage so as to be displaced by a pull from a generated friction of the rubber roller against said paper;

a back side of the paper holding device connected with a load cell fixed on said stage to reach a balance with the pull; and a set of different weights for selective engagement to said inserted pin, whereby said rubber roller is horizontally pressed against said one end of said paper and driven to rotate at a fixed speed to allow an accurate friction between said rubber roller and said support roller to be detected.

* * * * *